(12) United States Patent
Lee et al.

(10) Patent No.: US 7,842,916 B2
(45) Date of Patent: Nov. 30, 2010

(54) METHOD OF AND APPARATUS FOR ANALYZING IONS ADSORBED ON SURFACE OF MASK

(75) Inventors: Dong-Hun Lee, Gyeonggi-do (KR); Hae-Young Jeong, Gyeonggi-do (KR); Byung-Cheol Cha, Gyeonggi-do (KR); Sung-Jae Han, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 169 days.

(21) Appl. No.: 12/197,052

(22) Filed: Aug. 22, 2008

(65) Prior Publication Data

US 2009/0101811 A1    Apr. 23, 2009

(30) Foreign Application Priority Data

Aug. 24, 2007    (KR) ...................... 10-2007-0085576

(51) Int. Cl.
*G01N 33/00*    (2006.01)

(52) U.S. Cl. .................... 250/282; 250/281; 250/492.1; 156/345.13; 156/345.24; 436/73; 436/80; 436/150; 436/175; 436/704; 136/1.3; 136/30; 136/32; 136/40

(58) Field of Classification Search ........................ None
See application file for complete search history.

(56) References Cited

U.S. PATENT DOCUMENTS

| | | | | |
|---|---|---|---|---|
| 3,366,554 A | * | 1/1968 | Lindblad ..................... 205/791 |
| 4,023,931 A | * | 5/1977 | Wolfgram ................... 436/150 |
| 5,027,841 A | * | 7/1991 | Breunsbach et al. ....... 134/95.3 |
| 5,030,293 A | * | 7/1991 | Rich et al. .................... 134/32 |
| 5,234,506 A | * | 8/1993 | Winston et al. ............... 134/40 |
| 5,275,667 A | * | 1/1994 | Ganesan et al. ................ 134/1 |
| 5,294,280 A | * | 3/1994 | Wakabayashi et al. . 156/345.24 |
| 5,712,198 A | * | 1/1998 | Shive et al. .................. 438/745 |
| 5,783,099 A | * | 7/1998 | Huh ............................. 216/59 |
| 5,783,938 A | * | 7/1998 | Munson et al. ............ 324/71.2 |
| 5,994,142 A | * | 11/1999 | Yamasaki et al. ............. 436/73 |

(Continued)

FOREIGN PATENT DOCUMENTS

JP    11-101787    4/1999

(Continued)

OTHER PUBLICATIONS

English language abstract of Japanese Publication No. 11-101787.

(Continued)

*Primary Examiner*—David A Vanore
(74) *Attorney, Agent, or Firm*—Muir Patent Consulting, PLLC

(57) ABSTRACT

A method of analyzing ions adsorbed on a surface of a mask for pattern formation of a semiconductor device, and an apparatus using the same are disclosed. The ion analyzing method includes: filling a heating container within a main chamber with a predetermined amount of a solvent; immersing a mask in the solvent-filled heating container; raising an internal pressure of the chamber to a predetermined level by supplying gas into the chamber; separating ions from a surface of the mask by heating the solvent within the heating container at a predetermined temperature for a predetermined period; and analyzing the ions by collecting the solvent.

20 Claims, 3 Drawing Sheets

U.S. PATENT DOCUMENTS

| | | | |
|---|---|---|---|
| 6,150,175 A * | 11/2000 | Shelton et al. | 436/80 |
| 6,164,299 A * | 12/2000 | Sun et al. | 134/113 |
| 6,177,279 B1 * | 1/2001 | Sun et al. | 436/175 |
| 6,602,795 B2 * | 8/2003 | Gilton et al. | 438/745 |
| 6,635,590 B2 * | 10/2003 | Lee | 438/704 |
| 6,749,715 B2 * | 6/2004 | Gilton et al. | 156/345.13 |
| 7,144,486 B1 * | 12/2006 | Fritsch et al. | 204/403.06 |
| 7,276,454 B2 * | 10/2007 | Ching et al. | 438/745 |
| 2004/0038840 A1 * | 2/2004 | Lee et al. | 510/202 |
| 2004/0079395 A1 * | 4/2004 | Kim et al. | 134/30 |
| 2009/0065032 A1 * | 3/2009 | Han et al. | 134/61 |
| 2009/0101811 A1 * | 4/2009 | Lee et al. | 250/282 |
| 2010/0043823 A1 * | 2/2010 | Lee | 134/1.3 |

FOREIGN PATENT DOCUMENTS

| | | |
|---|---|---|
| JP | 2000-002632 | 1/2000 |
| KR | 2004-0050651 | 6/2004 |

OTHER PUBLICATIONS

English language abstract of Japanese Publication No. 2000-002632.
English language abstract of Korea Publication No. 2004-0050651.

* cited by examiner

METHOD OF AND APPARATUS FOR ANALYZING IONS ADSORBED ON SURFACE OF MASK

CROSS-REFERENCE TO RELATED PATENT APPLICATION

This application claims the benefit of Korean Patent Application No. 10-2007-0085576, filed on Aug. 24, 2007, in the Korean Intellectual Property Office, the disclosure of which is incorporated herein in its entirety by reference.

BACKGROUND OF THE INVENTION

1. Field of the Invention

The present invention relates to a method of and an apparatus for analyzing ions on a surface of a mask for semiconductor devices, and more particularly, to a method of and an apparatus for analyzing ions adsorbed on a surface of a mask using positive pressure effects.

2. Description of the Related Art

Circuit patterns on semiconductor devices are formed through a photolithography process. In such photolithography process, a photoresist film is deposited on a wafer, a pattern formed on a photomask is transcribed to the photoresist film by an exposure process, and the photoresist pattern is formed through a development process. Using the photoresist pattern, a film on the wafer is patterned to form a circuit pattern of the semiconductor device. In order to form the circuit pattern by the photolithography process, a mask, such as a photomask, is used. On a transparent substrate, such as light transmitting quartz, a shielding film such as light blocking chrome film is patterned on the photomask used for forming a circuit pattern in the photolithography process.

In order to manufacture a semiconductor device, an exposure process is carried out with many wafers using one photomask. When such repetitive photolithography process is carried out, unstable ions are produced during the process, and the unstable ions adsorb to a surface of the photomask by static electricity or chemical bonding. The ions adsorbed on the surface of the photomask not only prevent accurate transcription of the photomask pattern onto the wafers during photolithography process, but also produce identical repetitive defects on many wafers that are manufactured using the photomask.

Therefore, it is very important to remove the ions adsorbed on the surface of the photomask. Conventionally, ions adsorbed on surfaces of photomasks are removed by performing a cleaning process using sulfuric acid ($H_2SO_4$). While the cleaning process using sulfuric acid may remove the ions adsorbed on the surface of the photomask, sulfuric acid residues such as $SO_4^{2-}$ still remain on the photomask. In this regard, a method of removing the sulfuric acid residues by neutralization using ammonium hydroxide ($NH_4OH$) has been used, but such method produces salt such as $(NH_4)_2SO_4$ when neutralizing with $NH_4OH$.

Therefore, in order to remove the adsorbed ions on the surface of the photomask through a cleaning process, the ions adsorbed on the surface of the photomask must be accurately analyzed. Conventionally, ions on the surface of the photomask are collected and analyzed by ion chromatography (IC).

However, when using the conventional method for ion analysis, it is not only difficult to analyze ions accurately, but also the variation of analysis results is large, thereby making it difficult to determine the cleaning recipe for removing the ions. Moreover, a significant amount of time is spent on collecting the ions, thereby increasing the ion analysis time.

SUMMARY OF THE INVENTION

Example embodiments of the present invention provide a method of and an apparatus for analyzing ions adsorbed on a surface of a photomask using positive pressure effects to accurately analyze the ions adsorbed on the surface of the photomask, thereby obtaining superior reproducibility of the analysis results.

According to an aspect of the present invention, there is provided a method of analyzing ions adsorbed on a surface of a mask. First, a heating container within a chamber may be filled with a predetermined amount of a solvent. Then, a mask may be immersed in the solvent-filled heating container. An internal pressure of the chamber may be raised to a predetermined level by supplying gas into the chamber. The ions may be separated from the surface of the mask by heating the solvent within the heating container at a predetermined temperature for a predetermined period. The ions may then be analyzed by collecting the solvent.

The gas may include a purge gas, such as $N_2$, and the solvent may include deionized water. The amount of the solvent may be about 900 ml-1100 ml. The internal pressure of the chamber may be maintained at about 1-10 atm, and the temperature of the solvent may be kept at about 80-180° C. for about 5-10 minutes.

Example embodiments of the present invention also provide an apparatus for analyzing ions adsorbed to a surface of a mask. The ion analyzing apparatus may include a main chamber having a gas inlet for supplying gas inside the main chamber, a gas outlet for discharging gas from the main chamber, and a door through which a photomask enters and exits out of the main chamber; a heating container may be disposed in the main chamber and may be filled with a solvent to immerse the photomask in solvent; and a hot plate may be disposed in the main chamber, an upper surface of which may be communicatively coupled to the heating container.

The ion analyzing apparatus may further include a gas supply unit disposed outside of the main chamber, and configured to supply gas to the gas inlet of the main chamber in order to maintain a predetermined internal pressure in the main chamber.

The ion analyzing apparatus may further include a temperature controller disposed outside of the main chamber, and which controls the temperature of the hot plate.

The method of and the apparatus for analyzing ions according to example embodiments of the present invention use positive pressure effects to raise the boiling point of deionized water, which allows accurate separation of the ions adsorbed on a surface of the mask in a short time, thereby leading to accurate analysis results with superior reproducibility.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
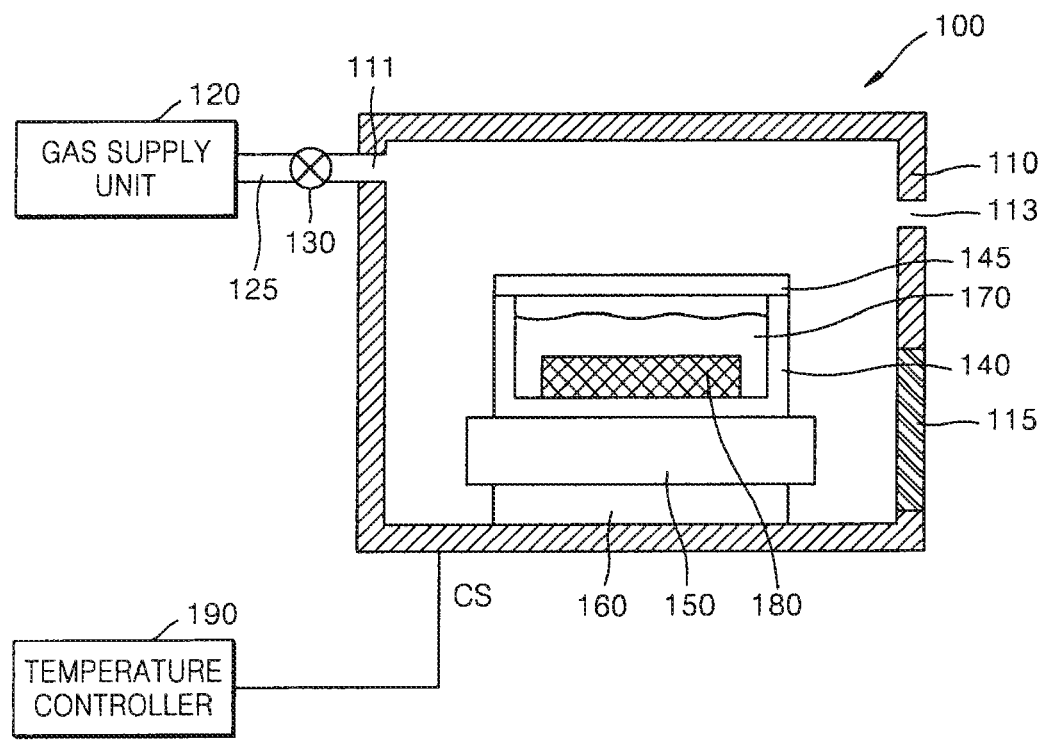
FIG. 1 is a cross-sectional view illustrating an apparatus for analyzing ions adsorbed on a surface of a mask, according to the embodiment of the present invention.

Hereinafter, the present invention will be described more fully with reference to the accompanying drawings, in which exemplary embodiments of the invention are shown. However, the embodiments described hereinafter are not intended to limit the scope of the present invention, and may be modified in other forms. The embodiments introduced here are provided to disclose the contents of the present invention more completely, and to sufficiently transfer the concept of the present invention to those of ordinary skill in the art. Therefore, figures of the components in the drawings and the like are exaggerated in order to emphasize a clear description. The same reference numbers represent the same components in the entire specification.

FIG. 1 is a schematic cross-sectional view of an ion analyzing apparatus according to the embodiment of the present invention. Referring to FIG. 1, an ion analyzing apparatus 100 includes a main chamber 110. The main chamber 110 includes on a sidewall a gas inlet 111 for supplying a purge gas, a gas outlet 113 for discharging the purge gas, and a door 115 through which a photomask 180 enters and exits from the main chamber 110. The purge gas may include $N_2$ gas. The purge gas is provided through the gas inlet 111 in order to cause the main chamber 110 to have a nitrogen atmosphere during ion sampling. Once the ion sampling is completed, nitrogen is purged through the gas outlet 113.

Although not shown in any drawings, the ion analyzing apparatus 100 may further include a subchamber as a buffer through which the photomask 180 enters or exits from the main chamber 110.

The ion analyzing apparatus 100 may further include a gas supply unit 120 disposed outside of the main chamber 110. The gas supply unit 120 supplies the purge gas to the gas inlet 111 through a gas channel 125 to raise the pressure in the main chamber 110 to a predetermined positive pressure. A solenoid valve 130 is disposed in the gas channel 125 such that gas supply from the gas supply unit 120 to the main chamber 110 may be controlled. Meanwhile, the gas outlet 113 may further include a gas channel (not shown) for gas discharge, and a solenoid valve (not shown) may further be disposed to control the gas discharge.

A hot plate 150 is disposed within the main chamber 110. The hot plate 150 may be disposed on a bottom portion of the main chamber 110. Alternately, in order to prevent contamination of the ions to be sampled, the hot plate 150 may be supported by a stand 160 such that the hot plate 150 is placed at a predetermined distance from the bottom portion of the main chamber 110.

A heating container 140 is disposed on the hot plate 150. The heating container 140 is composed of a quartz material. The heating container 140 may be covered by a lid member 145. The lid member 145 may include a quartz material. A solvent such as deionized water 170 may be contained within the heating container 140. A photomask 180 may be immersed in the deionized water 170 in the heating container to analyze the adsorbed ions.

It is desirable that the photomask 180 be immersed in the deionized water 170 without overflowing the heating container 140. For example, a predetermined amount of the deionized water 170 may be about 900-1100 ml. The deionized water 170 may be contained in the heating container 140 and heated through the hot plate 150 at a predetermined temperature, such as about 80-180° C.

The ion analyzing apparatus 100 may further include a temperature controller 190 which controls the temperature of the hot plate 150, in order to control the boiling point of the deionized water 170 within the heating container 140. The temperature controller 190 may be disposed outside of the main chamber 110, and may provide a control signal CS to control the temperature of the hot plate 150.

Figure 2:
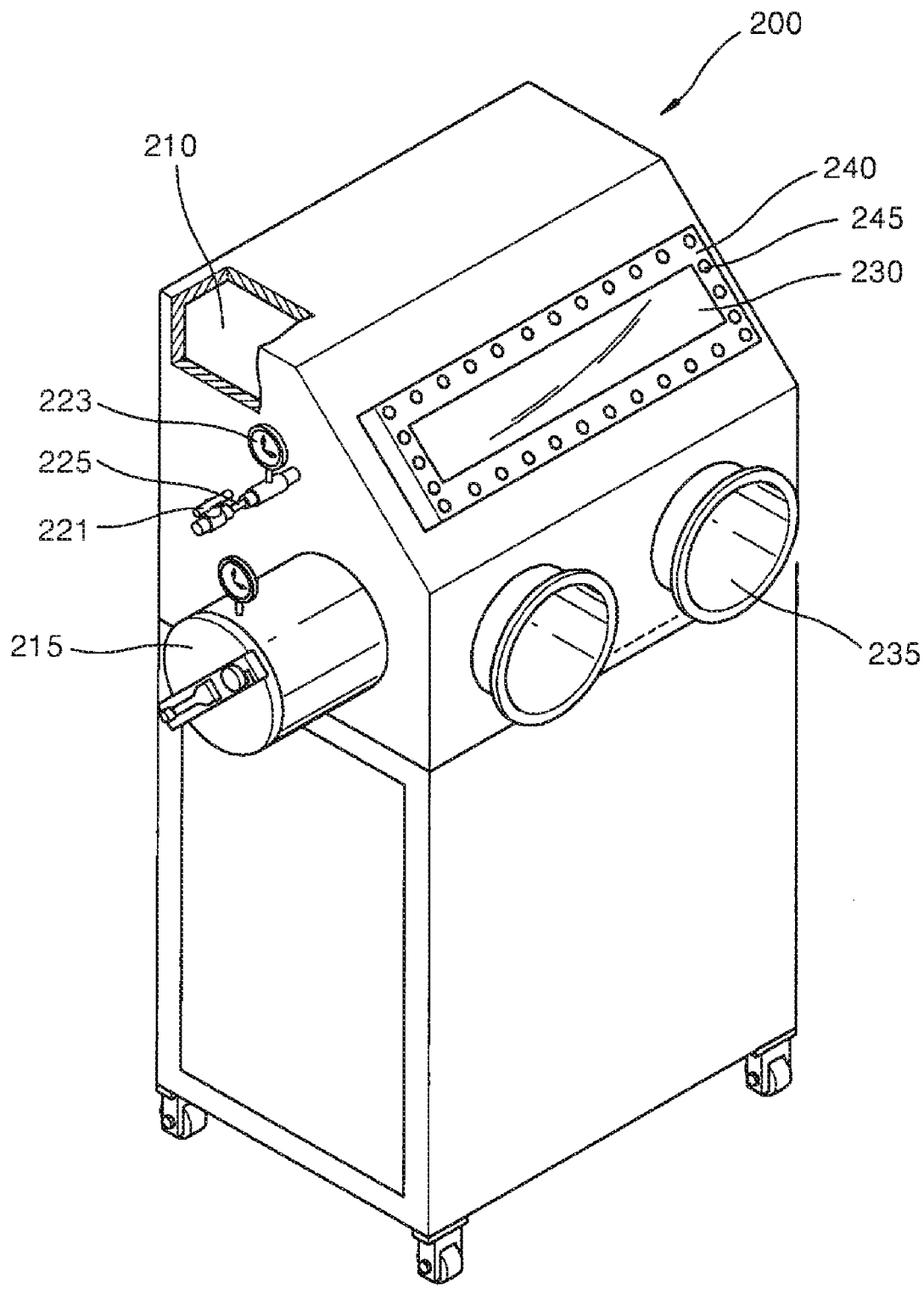
FIG. 2 is a perspective view illustrating a semiconductor testing apparatus including the ion analyzing apparatus of FIG. 1, according to an embodiment of the present invention.

FIG. 2 is a perspective view illustrating a semiconductor testing apparatus according to an embodiment of the present invention. Referring to FIG. 2, a semiconductor testing apparatus 200 includes the ion analyzing apparatus 100 of FIG. 1, and may also include an apparatus to test semiconductor devices under a nitrogen atmosphere.

The semiconductor testing apparatus 200 includes a chamber 210, which corresponds to the main chamber 110 of FIG. 1. Inside the chamber 210, as shown in FIG. 1, a heating container 140 may be disposed on the hot plate 150, and the heating container 140 may be filled with deionized water 170 such that the photomask 180 for ion analysis can be immersed in the deionized water.

In an upper part of another wall of the semiconductor testing apparatus 200, a window 230 through which the inside of the chamber 210 can be seen with the naked eye is disposed. The window 230 may be fixed by a fixing member 240 made of metallic plate material. The fixing member 240 may be fastened by a fastening element 245 such as a screw. Gloves 235 may be arranged in a lower portion of the outer wall of the chamber below the window 230. It is desirable that the gloves 235 be arranged corresponding to the heating container arranged inside the chamber 210.

Moreover, a gas channel 225, which corresponds to the gas channel 125 of FIG. 1, may be installed on an outer wall of the chamber, and a valve 221, which corresponds to the solenoid valve 130 of FIG. 1, may be installed in the gas channel 225. In addition, a gauge 223 that can display the amount of gas supplied to the chamber 210 may be installed in the gas channel 225. The gas channel 225 may be connected to the gas supply unit 120 as in FIG. 1. Furthermore, a gas outlet may be disposed in the chamber 210.

Additionally, a door 215, which corresponds to the door 115 of FIG. 1, may be arranged in the outer wall below the gas channel 223 so that the photomask 180 can enter and exit from the chamber 210.

Figure 3:
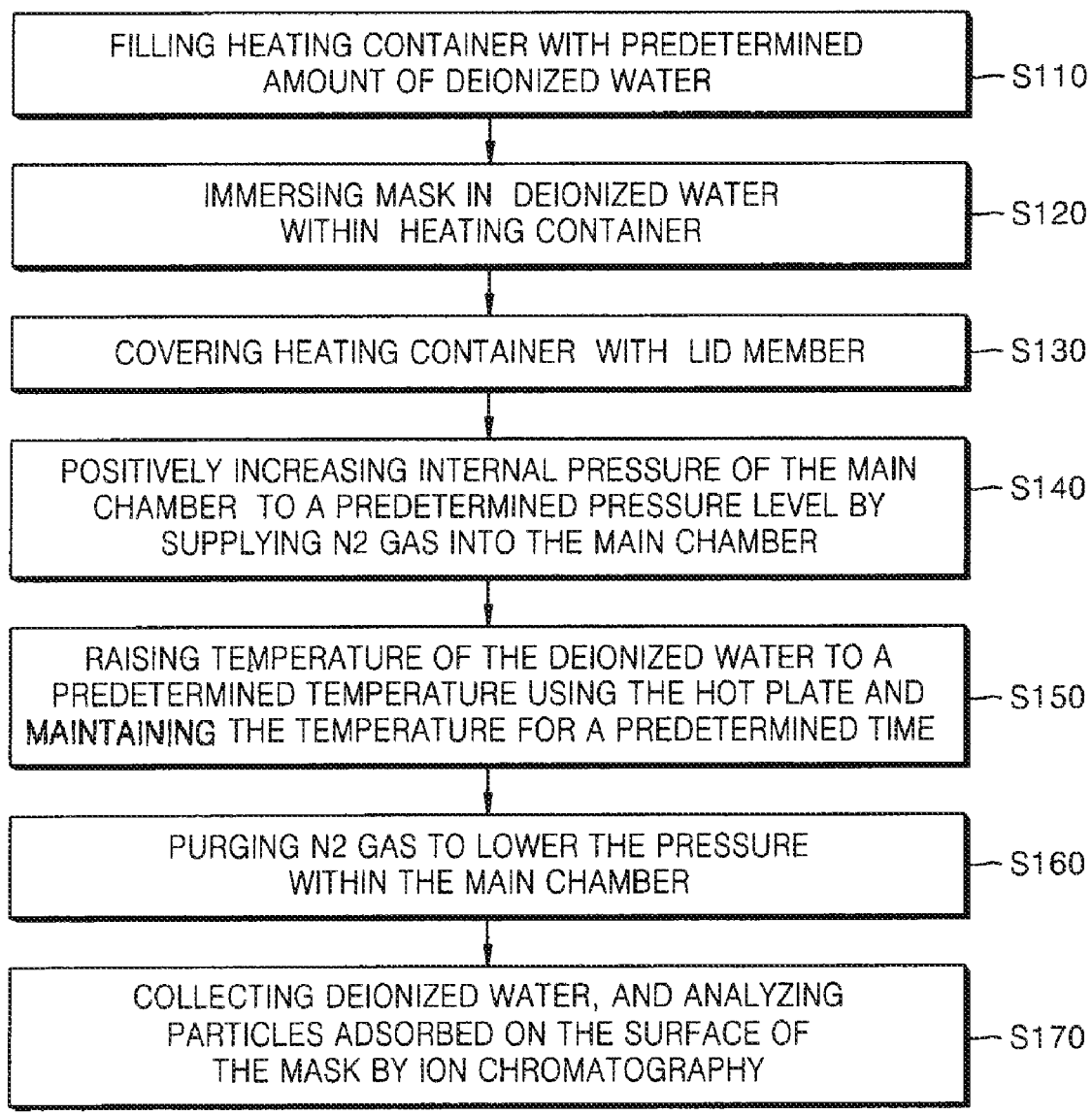
FIG. 3 is a flow diagram of a method of analyzing ions adsorbed on a surface of a mask using the ion analyzing apparatus of FIG. 1, according to an embodiment of the present invention.

FIG. 3 is a flow diagram of a method of analyzing ions adsorbed on the surface of the photomask using the ion analyzing apparatus 100 of FIG. 1.

First, the heating container 140 is disposed on the hot plate 150 within the main chamber 110 of the ion analyzing apparatus 100. A predetermined amount of the solvent 170 is added to the heating container 140 (S110). The solvent 170 may include deionized water. The solvent 170 is sufficiently filled in the heating container 140 such that the photomask 180 is completely immersed therein, while not letting the solvent 170 overflow from the heating container 140 during heating. For example, about 900-1100 ml of the solvent 170 is contained in the heating container 140.

The photomask 180 is transported through the door 115 of the main chamber 110, and immersed in the heating container 140 filled with the solvent 170 (S120). The heating container 140 is covered with the lid member 145 (S130). The door 115 of the main chamber 110 is locked such that the inside of the main chamber 110 is isolated from external air.

Sequentially, the purge gas is supplied from the gas supply unit 120 to the gas inlet 111 of the main chamber 110 through the gas channel 125, thereby raising the pressure in the main chamber 110 to a predetermined level (S140). The purge gas may include $N_2$ gas. Therefore, the inside of the main chamber 110 is maintained at a predetermined positive pressure. The internal pressure in the main chamber 110 may be maintained at about 1-10 atm.

While the main chamber 110 is maintained at the predetermined positive pressure, the heating container 140 is heated using the hot plate 150 to keep the solvent 170 at a predetermined temperature for a predetermined time. The temperature 170 of the solvent may be maintained at about 80-180° C. for about 5-10 minutes.

The solvent 170. which may be deionized water, comes to a boil in the heating container 140 at about 100° C. when the internal pressure of the main chamber 110 is about 1 atm. As the pressure rises, the boiling point of the deionized water increases, and as the pressure drops, the boiling point decreases.

When the internal pressure of the main chamber 110 is positively increased and the solvent 170 in which the photomask 180 for ion measurement is immersed is heated using the hot plate 150, the boiling point of the solvent 170 increases with the internal pressure of the main chamber. There is a binding energy between a film photomask 180 and the ions adsorbed on the surface of the film. The binding energy is weakened as the temperature of the solvent 170 in which the photomask 180 is immersed rises, thereby allowing easy separation of the ions adsorbed on the surface of the photomask 180. Therefore, when the internal pressure of the main chamber 110 is positively increased to sufficiently raise the temperature of the solvent 180 to the point that the bond between the film photomask 180 and the adsorbed ions is broken, the ions adsorbed on the surface of the photomask 180 are separated from the photomask 180 and dissolved in the solvent 170.

The purge gas within the main chamber 110 may be discharged through the gas outlet 113 to decrease the internal pressure of the main chamber 110 to the original state (S160). The solvent 180 is collected and the ions adsorbed on the photomask 180 may be analyzed using ion chromatography (S170).

In some example embodiments of the present invention, the ions adsorbed on the surface of the photomask are completely separated from the photomask and dissolved in deionized water by sufficiently increasing the temperature of the solvent, thereby allowing an accurate analysis of the ions and a decrease in the variation of the analysis results. Example embodiments of the present invention provide an efficient determination of an accurate cleaning recipe. Moreover, by sufficiently separating the ions adsorbed on the surface of the photomask in a very short time, the ion analysis time can be shortened.

While the present invention has been particularly shown and described with reference to exemplary embodiments thereof, it will be understood by those of ordinary skill in the art that Various changes in form and details may be made therein without departing from the spirit and scope of the present invention as defined by the following claims.

What is claimed is:

1. A method of analyzing ions adsorbed on a surface of a mask, comprising:

filling a heating container within a chamber with a predetermined amount of a solvent;

immersing a mask in the solvent-filled heating container;

raising an internal pressure of the chamber to a predetermined level;

separating ions from a surface of the mask by heating the solvent within the heating container to a predetermined temperature for a predetermined period; and analyzing the ions by collecting the solvent.

2. The method of claim 1, wherein the solvent is deionized water.

3. The method of claim 2, wherein the amount of the solvent filled in the heating container is about 900-1100 ml.

4. The method of claim 1, further comprising maintaining the internal pressure of 20 the chamber at about 1-10 atm.

5. The method of claim 4, further comprising maintaining the temperature of the solvent at about 80-180° C.

6. The method of claim 5, further comprising maintaining the temperature of the solvent for about 5-10 minutes.

7. The method of claim 1, further comprising covering the heating container with a lid member between immersing the mask into the solvent and raising the internal pressure of the chamber.

8. The method of claim 1, further comprising analyzing the ions using ion chromatography.

9. The method of claim 1, wherein separating ions from the surface of the mask includes substantially completely separating the ions adsorbed on the surface of the mask from the mask.

10. The method of claim 9, wherein separating ions from the surface of the mask includes dissolving the separated ions in the solvent by increasing the temperature of the solvent.

11. The method of claim 1, wherein raising the internal pressure further comprises supplying a gas into the chamber.

12. The method of claim 11, wherein the gas is a purge gas.

13. The method of claim 11, further comprising discharging the gas from the chamber between separating the ions from the surface of the mask and collecting the solvent.

14. The method of claim 12, wherein the purge gas is $N_2$.

15. The method of claim 1, further comprising controlling the heating of the solvent with a temperature controller.

16. The method of claim 1, further comprising providing a hot plate within the chamber under the heating container.

17. A method of manufacturing, comprising:

adding a solvent to a heating container within a chamber;

immersing a mask in the solvent within the heating container;

raising an internal pressure of the chamber;

separating ions from a surface of the mask by heating the solvent within the heating container; and manufacturing a semiconductor device using the mask.

18. The method of claim 17, wherein the solvent is deionized water.

19. The method of claim 17 wherein the internal pressure of the chamber is raised to about 1-10 atm.

20. The method of claim 17, wherein the temperature of the solvent is heated to about 80-180° C.

* * * * *